(12) United States Patent
Humbert et al.

(10) Patent No.: US 9,453,807 B2
(45) Date of Patent: Sep. 27, 2016

(54) THERMAL CONDUCTIVITY GAS SENSOR WITH AMPLIFICATION MATERIAL

(71) Applicant: ams International AG, Rapperswil-Jona (CH)

(72) Inventors: Aurelie Humbert, Brussels (BE); Dimitri Soccol, Rotselaar (BE); Roel Daamen, Herkenbosch (NL); Annelies Falepin, Hoegaarden (BE)

(73) Assignee: AMS INTERNATIONAL AG, Rapperswil-Jona (CH)

( * ) Notice: Subject to any disclaimer, the term of this patent is extended or adjusted under 35 U.S.C. 154(b) by 144 days.

(21) Appl. No.: 14/248,102

(22) Filed: Apr. 8, 2014

(65) Prior Publication Data
US 2015/0285750 A1 Oct. 8, 2015

(51) Int. Cl.
G01N 25/18 (2006.01)
G01N 33/00 (2006.01)
G01N 25/36 (2006.01)
G01N 27/18 (2006.01)

(52) U.S. Cl.
CPC .............. G01N 25/18 (2013.01); G01N 27/18 (2013.01); G01N 33/004 (2013.01); G01N 25/36 (2013.01); G01N 27/185 (2013.01)

(58) Field of Classification Search
CPC ..... G01N 27/185; G01N 27/18; G01N 25/18
USPC ....... 73/25.03, 25.01, 23.2; 374/28; 257/417
See application file for complete search history.

(56) References Cited

U.S. PATENT DOCUMENTS

| 4,215,564 A | 8/1980 | Lawson |
| 4,349,808 A | 9/1982 | Kraus |
| 4,580,439 A | 4/1986 | Manaka |
| 4,967,589 A | 11/1990 | Yagawara et al. |
| 5,143,696 A | 9/1992 | Haas et al. |
| 5,448,905 A * | 9/1995 | Stetter ................ G01N 33/0049 73/23.21 |
| 5,597,953 A | 1/1997 | Usanov et al. |
| 5,753,916 A | 5/1998 | Ooisi et al. |
| 5,756,878 A | 5/1998 | Muto et al. |
| 6,238,085 B1 * | 5/2001 | Higashi .................. G01N 25/18 374/10 |
| 7,564,350 B2 | 7/2009 | Boman et al. |

(Continued)

FOREIGN PATENT DOCUMENTS

| CN | 101578188 A | 11/2009 |
| CN | 201341166 Y | 11/2009 |

(Continued)

OTHER PUBLICATIONS e2v; "Pellistor Application Note 5—Thermal Conductivity Sensors"; e2v technologies (uk) limited, Waterhouse Lane, Chelmsford, Essex CM1 2QU, UK; 2 pages (Mar. 2007).

(Continued)

Primary Examiner — Lisa Caputo
Assistant Examiner — Nathaniel T Woodward
(74) Attorney, Agent, or Firm — McDermott Will & Emery LLP

(57) ABSTRACT

In one example, a thermal conductivity gas sensor is disclosed. The sensor includes a sensing element and an amplification material coupled to the sensing element. The amplification material has a target gas dependent thermal diffusivity. The sensing element measures the thermal diffusivity of the amplification material to determine a target gas concentration.

13 Claims, 3 Drawing Sheets

(56) References Cited

U.S. PATENT DOCUMENTS

| | | | |
|---|---|---|---|
| 7,574,910 B2 | 8/2009 | Manaka et al. | |
| 7,628,907 B2 * | 12/2009 | Gu | G01N 33/004 204/424 |
| 7,670,046 B2 | 3/2010 | Mitov | |
| 8,161,795 B2 | 4/2012 | De Coulon et al. | |
| 8,303,788 B2 * | 11/2012 | Williamson | G01N 27/404 204/415 |
| 8,393,196 B2 | 3/2013 | Ikawa et al. | |
| 8,452,489 B2 | 5/2013 | Marra | |
| 8,853,798 B2 | 10/2014 | Merz | |
| 2004/0025117 A1 | 2/2004 | Ingersoll et al. | |
| 2006/0154401 A1 * | 7/2006 | Gardner | G01N 27/128 438/53 |
| 2006/0169024 A1 | 8/2006 | Shoji | |
| 2008/0311434 A1 | 12/2008 | Rey-Mermet et al. | |
| 2013/0032902 A1 | 2/2013 | Merz | |
| 2013/0042669 A1 | 2/2013 | Humbert et al. | |
| 2013/0295680 A1 | 11/2013 | Yaghi et al. | |
| 2013/0327989 A1 | 12/2013 | Jessop et al. | |
| 2014/0102172 A1 | 4/2014 | Daamen et al. | |

FOREIGN PATENT DOCUMENTS

| | | | | |
|---|---|---|---|---|
| CN | 102054303 A | 5/2011 | | |
| DE | 10 2006 009 450 A1 | 9/2006 | | |
| EP | 0498063 A2 * | 8/1992 | | G01N 25/482 |
| EP | 1643241 A2 | 4/2006 | | |
| EP | 2224231 A1 | 9/2010 | | |
| EP | 2693207 A1 | 2/2014 | | |
| EP | 2 743 667 A1 | 6/2014 | | |
| EP | 2 853 889 A1 | 4/2015 | | |
| JP | 6 118046 | 12/1995 | | |
| JP | 2005/003468 A | 1/2005 | | |
| WO | 2005/069597 A1 | 7/2005 | | |
| WO | 2009/138893 A1 | 11/2009 | | |

OTHER PUBLICATIONS

Microsens SA; "Microsens Thermal Conductivity Sensor—MTCS-2202, Natural Gas (Methane) Sensor"; Switzerland; 4 pages.
Hach; "Orbisphere TC Sensor Selective Gas Measurement"; Technical Data; 2 pages (Dec. 2009).
Datasheet, "NAP-21A", Nemoto & Co., Ltd., retrieved from the Internet on Jul. 18, 2012 at http:/ /www.nemoto.co.jp/en/products/sensor/manual/nap-21a.html, 1 pg. (2008).
Research Institute of Innovative Technology for the Earth; "Development of New Amine Absorbents in COCS project"; Lyon, France; 17 pages (May 24, 2007).
Neda, T., et al; "A Polysilicon Flow Sensor for Gas Flow Meters"; Tranducers '95, Eurosensors IX; 8th Intl. Conf. on Solid-State Sensors and Actuators and Eurosensors IX; Stockholm, Sweden, Jun. 25-29, 1995; 4 pages.
POSiFA Microsystems Inc; "Thermal Conductivity Gas Sensor Die"; 3 pages retrieved from the internet Apr. 8, 2014 http://www.posifamicrosystems.com/pdf/2012-30-20-01-10_PTCD10-Data-Sheet_20120116.pdf.
Nemoto Sensor Engineering Co., Ltd.; "Residential Sensors—NAP-21A"; Tokyo, JP; 1 page (Nov. 2012).
Barth, R., et al; "High-$T_c$ air-bridge microbolometers fabricated by silicon micromachining technique"; Elsevier, Microelectronic Engineering 27; pp. 499-502 (1995).
Gattuso, Stephen A.; "Carbon Dioxide Capture by Tertiary Amidine Functional Adsorbents"; Thesis, Duquesne University; 66 pages (2003).
Lili, Liu et al., "Coal Mine Security IntelligentControl System Based on RFID", retrieved from the internet www.cnki.net, pp. 39-41, Sep. 2004, no English version available.

* cited by examiner

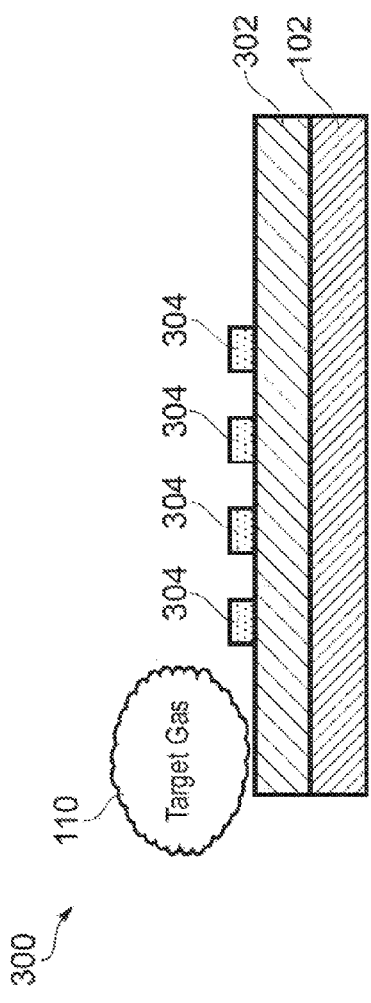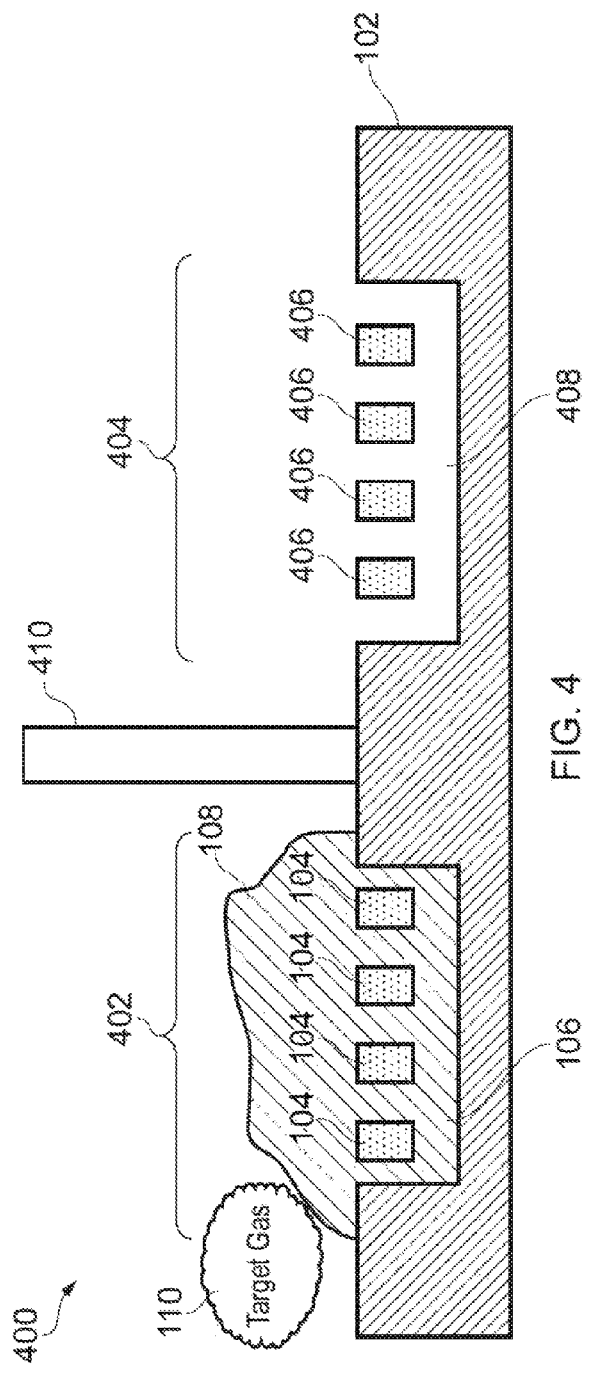

THERMAL CONDUCTIVITY GAS SENSOR WITH AMPLIFICATION MATERIAL

CROSS-REFERENCE TO RELATED OR CO-PENDING APPLICATIONS

This application may relate to and incorporates by reference co-pending U.S. patent application Ser. No. 13/557,042 entitled "Gas Sensor", filed on Jul. 24, 2012, by Humbert et al., and Published as US20130042669 A1 on Feb. 21, 2013. This potentially related application is assigned to NXP B.V. of Eindhoven, Netherlands.

BACKGROUND

Brief Background Introduction

This specification relates generally to systems and methods for sensing a gas, and in one example to sensing a concentration of a target gas, such as carbon dioxide.

SUMMARY

A gas sensor, comprising: a sensing element; and an amplification material coupled to the sensing element, and having a target gas dependent thermal diffusivity; wherein the sensing element measures the thermal diffusivity of the amplification material.

The above summary is not intended to represent every example embodiment within the scope of the current or future Claim sets. Additional example embodiments are discussed within the Figures and Detailed Description below.

BRIEF DESCRIPTION OF THE DRAWINGS

FIG. 3 is a third example of a gas sensor.
FIG. 4 is a fourth example of a gas sensor paired with a matched gas sensor.

Figure 1:
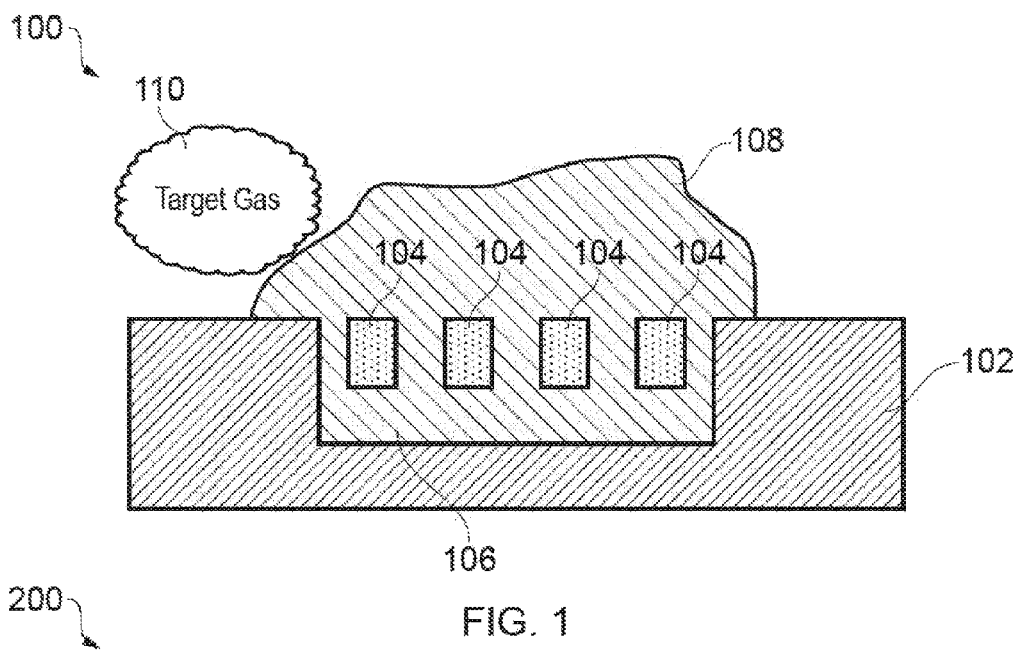
FIG. 1 is a first example of a gas sensor.

While the disclosure is amenable to various modifications and alternative forms, specifics thereof have been shown by way of example in the drawings and will be described in detail. It should be understood, however, that other embodiments, beyond the particular embodiments described, are possible as well. All modifications, equivalents, and alternative embodiments falling within the spirit and scope of the appended claims are covered as well.

DETAILED DESCRIPTION

A thermal conductivity gas sensor, also known as hot wire detector, operates on the principle that gases differ in their ability to conduct heat. This property is used for measuring gas concentration in mixtures where component gases have different thermal conductivity. Such gas sensors can be used in a number of different applications to sense the composition and/or concentration of various gases. One example application is in the field of supply chain monitoring, in which a level of carbon dioxide (CO2) present in the air surrounding consumables such as food or beverages is monitored to determine suitability for consumption. The monitoring may typically be carried out at various stages in the distribution chain. Other applications include air quality monitoring, use in heating, ventilation and air conditioning (HVAC) system in buildings or automobiles, or CO2 monitoring in a greenhouse.

The gas sensor configuration in one example consists of a heating element and a sensing element although the heater and the sensing element can be the same element. One example sensor consists of a filament of platinum or tungsten wire exposed to a gas and heated by an electrical current. In other common configurations, the sensor die consists of two thin-film resistors, the first one responds to target gas concentration variation, and the second is used for compensation of other external ambient changes (e.g. external temperature).

Calibration of a thermal conductivity gas sensor may begin by first heating the sensor until thermal equilibrium in the presence of a reference gas. After calibration the sensor is exposed to one or more target gases to be measured. The thermal equilibrium temperature of the gas sensor then increases or decreases depending on the target gases' thermal conductivity relative to that of the reference gas. The temperature change in one example results in a resistance change in the measurement element that is measured with a circuit to produce a digital reading proportional to the gas concentration.

Direct contact between the gas sensor's sensing element and the target gases can provide a percentage level accuracy; however, small ppm variations (~50 ppm) for smart building applications for example, require greater accuracy. Also, since the thermal conductivity of some target gases can be very similar to the thermal conductivity of the total gas mixture received measuring small changes in target gas concentration can be challenging. For example the thermal conductivity of CO2 is similar to the thermal conductivity of the main component of air (e.g. nitrogen). Cross sensitivities with relative humidity, temperature, pressure and gas flow rate can also add noise to the target gas concentration measurement.

Now described is an example gas sensor structure, which combines a thermal diffusivity measurement and an amplification material sensitive to a target gas, thereby enhancing a performance of the sensor in terms of sensitivity and cross sensitivity management. Using the amplification material, the sensing element in the gas sensor can be better tuned to a particular target gas, instead of being uniformly exposed to all gases in a received gas flow. Such tuning increases the gas sensor's sensitivity (e.g. amplifies sensitivity to the target gas) enabling better ppm detection especially for target gases such as CO2 which have a thermal conductivity only slightly different than air.

The amplification material may interact with the target gas in a variety of ways, including: a reversible chemical reaction of the target gas with the material, or by an irreversible absorption of the target gas in the material.

Use of the amplification material around all or a portion of the sensing element also helps isolate the sensing element from cross sensitivities due to relative humidity, temperature, gas pressure, and gas flow rate. Such amplification material, properly positioned can also create a more stable mechanical structure which can be useful in particularly turbulent gas flows (e.g. no free-hanging wires over a cavity).

Thus the thermal conductivity structure will not sense the target gas (e.g. CO2) concentration directly from the received gas flow, but will sense it via an indirect mechanism involving an interaction between the target gas and the amplification material. As the amplification material reacts with the target gas, the amplification material will induce a stronger effect than just probing for the target gas in the received volume of gas. In other example embodiments, the amplification material can also be selected to be more reactive to the target gas and less reactive to relative humidity, thereby reducing cross sensitivities to relative humidity or other gases present in the received gas flow.

FIG. 1 is a first example of a gas sensor 100. The gas sensor 100 can be a thermal conductivity gas sensor, including a sensing element 104 and an amplification material 108 located within a cavity 106 on a semiconductor substrate 102, and fabricated using CMOS processes. In one example, the amplification material 108 chemically or molecularly attracts a target gas 110 (e.g. concentrates the target gas) more than the sensing element 104.

The amplification material 108 is shown encapsulating (e.g. covering) the sensing element 104 (e.g. a sensing wire). In an alternate example the amplification material 108 does not encapsulate the whole sensing element 104, but rather is just in contact with one or more portions of the sensing element 104. The amplification material 108 has a thermal diffusivity which is dependent upon a target gas 110. In one example the target gas 110 is carbon dioxide (CO2).

The sensing element 104 is used to measure the thermal diffusivity of the amplification material 108. The thermal diffusivity measurement is then translated into a target gas concentration. Thermal diffusivity $\alpha$ is defined as $\alpha = k/(\rho \ast Cp)$, where k is heat conductivity, $\rho$ is density and Cp is heat capacity. Cp, k and $\rho$ can individually increase or decrease by absorbing or reacting with the target gas 110.

The sensing element 104 is electrically connected to a module (not shown) which calculates a target gas concentration based on the thermal diffusivity measurements from the sensing element 104. The module can be either a dedicated circuit, a firmware or software program, or some combination of the two. In one example the gas sensor 100 is heated with by passing a current through either the sensing element 104 or a separate heating element (not shown). Once the gas sensor 100 has reached a thermal equilibrium sensing element 104 measurements are taken.

Depending on how the amplification material 108 reacts with the target gas, at least three modes of gas sensor 100 operation are possible.

In a First Mode the target gas reversibly modifies the thermal diffusivity of the amplification material 108. Reversible modification is herein defined as a property which permits the amplification material 108 to both absorb and/or react and expel the target gas 110 without requiring any additional energy input.

In a Second Mode the target gas irreversibly modifies the thermal diffusivity of the amplification material 108, after which the thermal diffusivity of the amplification material 108 needs to be reset to an initial thermal diffusivity by heating the amplification material 108 either with a separate heating element or with the sensing element 104.

In one example, quickly heating the sensing element 104 to a relatively high temperature (higher than the normal operating temperature where thermal diffusivity is determined) will release the captured target gas 110 (e.g. CO2) from the saturated amplification material 108. In this mode, both the thermal diffusivity change and the absolute value of the thermal diffusivity are monitored. Once the amplification material 108 is saturated with the target gas 110, regeneration by heat or another technique will reset the material 108.

In a Third Mode the target gas irreversibly modifies the thermal diffusivity of the amplification material 108, and the above mentioned module calculates a target gas concentration based on an amount of heat energy required to reset the thermal diffusivity of the amplification material 108 to an initial thermal diffusivity. This technique monitors the total heat consumption (calorimetry) and the heat flow during the regeneration step. The amount of energy required for reversing an irreversible reaction (=regeneration) is directly proportional to the amount of target gas 110 that has reacted with the amplification material 108 between two consecutive regeneration steps. This will provide a second measure of the gas concentration.

While the First mode in one example may use less energy, the Second and Third modes can operate with a much wider range of amplification materials.

In one example the amplification material 108 is at least one from a group consisting of: a single amine solvent, a blended amine solvent, and polymer or metal-organic frameworks having an increase in target gas molar density compared to a molar density of the target gas in air.

Some example amplification materials 108 which interact with carbon dioxide are now listed. These materials either reversibly react with CO2 or irreversibly capture CO2. The irreversible capture is mostly with chemical bonds and can be reversible when the amplification material 108 are heated.

These example amplification materials 108 include over one hundred organic bases molecules, such as:
Primary amines
Secondary amines
Tertiary amines
Piperazine
Piperidine (PR)
Poly-alykylene poly-amines (TEPA, etc)
Amidines Alternatively, blended amine solvents, such as a mixture of 2 or 3 amines with different features can be used.

Also liquid solvents, or polymers and metal-organic frameworks that show an increase in $CO_2$ molar density compared to the $CO_2$ molar density in air can be used, such as:
Polymer absorbing CO2
Polymer chemically reacting to CO2
Zeolites
MOF In one example the thermal diffusivity of the amplification material 108 selected to vary more when exposed to the target gas, than does a thermal diffusivity of a received gas containing the target gas, thereby increasing the sensitivity of the gas sensor 100 to the target gas 110.

A more specific example of a gas sensor 100 where the sensing element 104 is a resistive transducer is now discussed. In this example, the sensing element 104 has a first resistance when the amplification material 108 is exposed to a reference gas and a second resistance when the amplification material 108 is exposed to a target gas. The circuit or software module (discussed earlier) then converts a difference between the first resistance and the second resistance into a target gas concentration. The module may additionally include a timing device (not shown) which provides for a concentration or integration time for the target gas 110 to react with the amplification material 108.

In this specific example, the measurement technique is a constant temperature (e.g. constant resistance) method. In these methods, the drive current (I) or voltage (V) is adapted as the target gas concentration varies. Then I or V as a function of target gas concentration is monitored. A constant power method could also be used where an applied input power is kept constant as the target gas concentration varies and $\Delta R/R$ is then monitored. Alternatively, the heater temperature can be swept by increasing the power and simultaneously tracking its resistance. Using this technique, the heat dissipated to the environment as a function of temperature will be known and a DSC measurement (Differential Scanning calorimetry) can be used to then determine the actual target gas concentration.

In other examples the sensing element 104 is either a capacitive transducer, an impedance transducer, or an optical transducer, each of which take measurements that the module translates into target gas concentrations.

Figure 2:
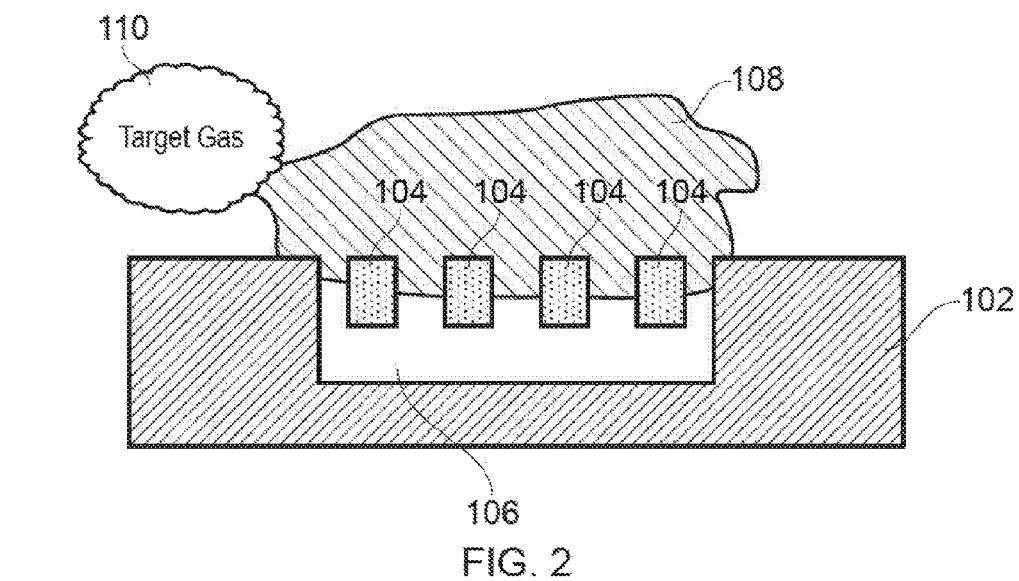
FIG. 2 is a second example of a gas sensor.

FIG. 2 is a second example of a gas sensor 200. In this example, the sensing element 104, amplification material 108, cavity 106 and semiconductor substrate 102 are as described in FIG. 1. One difference from FIG. 1 is that in one example the amplification material 108 does not fully encapsulate (e.g. cover) the sensing element 104 (e.g. a sensing wire). Another difference from FIG. 1 is that in another example the amplification material 108 is deposited on top of the sensing element 104 (e.g. thermal conductivity electrodes) and seals the top of the cavity 106.

FIG. 3 is a third example of a gas sensor 300. In this example, a silicon substrate 102 is first covered by an amplification material 302. A sensing element 304 is then fabricated on a side of the amplification material 302 opposite to the substrate 102. Thus the sensitive material (i.e. the amplification material 302) is deposited below the thermal conductivity electrodes (i.e. the sensing element 304).

FIG. 4 is a fourth example 400 of a gas sensor 402 paired with a matched gas sensor 404. The matched gas sensor 404 includes a sensor element 406 formed within a cavity 408 in the substrate 102. The gas sensor 402 is similar to the gas sensor 100 discussed in FIG. 1, however, the matched gas sensor 404 functions as a duplicate reference thermal conductivity structure which is not exposed to the target gas 110 (i.e. separated from the target gas 110 by a barrier 410). The matched gas sensor 404 is used to compensate for other types of gas sensor 402 sensitivity (e.g. relative humidity, gas pressure, gas flow and so on).

Figure 5:
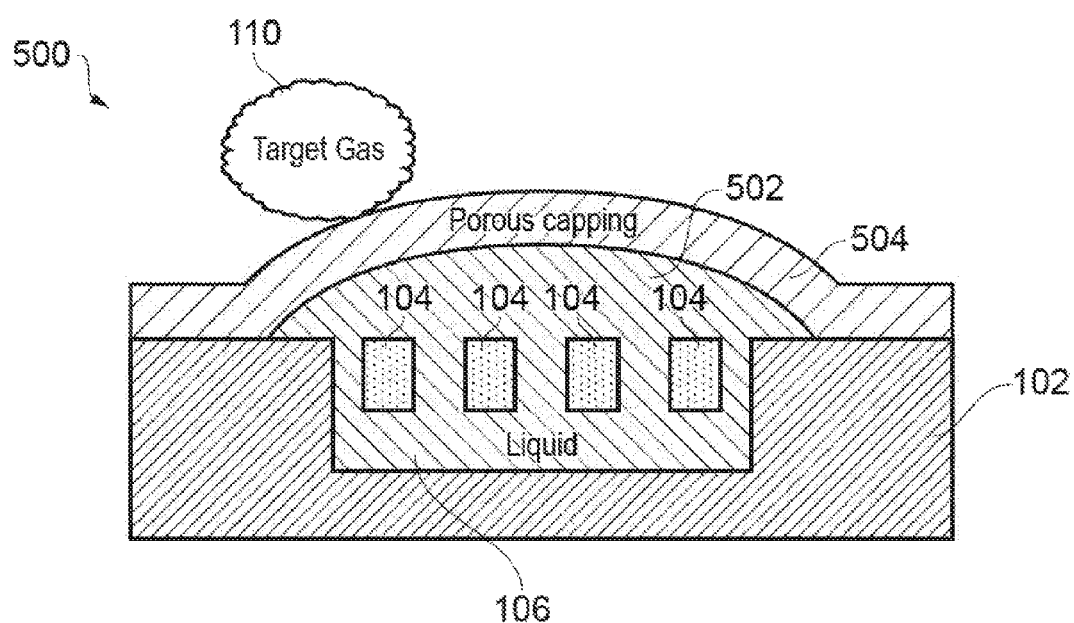
FIG. 5 is a fifth example of a gas sensor.

FIG. 5 is a fifth example of a gas sensor 500. In this example, the sensing element 104, cavity 106 and semiconductor substrate 102 are as described in FIG. 1. One difference from FIG. 1 is that in this example gas sensor 500 a liquid amplification material 502 encapsulates all or a portion of the sensing element 104. A cap material 504 porous to the target gas 110 keeps the liquid amplification material 502 in partial or total contact with the sensing wire 104.

In this specification, example embodiments have been presented in terms of a selected set of details. However, a person of ordinary skill in the art would understand that many other example embodiments may be practiced which include a different selected set of these details. It is intended that the following claims cover all possible example embodiments.

What is claimed is:

1. A thermal conductivity gas sensor, comprising:
   a sensing element;
   an amplification material coupled to the sensing element, and having a target gas dependent thermal diffusivity; and
   a semiconductor substrate having a cavity, the sensing element being positioned within the cavity,
   wherein the sensing element measures the thermal diffusivity of the amplification material,
   wherein the amplification material is positioned around all of the sensing element such that the amplification material encapsulates the sensing element, and
   wherein the sensing element is a resistive transducer such that the sensing element has a first resistance when the amplification material is exposed to a reference gas and a second resistance when the amplification material is exposed to a target gas.

2. The sensor of claim 1, further comprising:
   a module which calculates a target gas concentration based on the thermal diffusivity measurement,
   wherein the sensing element is electrically connected to the module.

3. The sensor of claim 1, wherein the thermal diffusivity of the amplification material varies more when exposed to a received gas containing the target gas, than does the thermal diffusivity of the received gas varies when exposed to the target gas.

4. The sensor of claim 1, wherein the target gas reversibly modifies the thermal diffusivity of the amplification material.

5. The sensor of claim 4, wherein the thermal diffusivity of the amplification material is reset to an initial thermal diffusivity by heating the sensing element.

6. The sensor of claim 4, further comprising:
   a module which calculates a target gas concentration based on an amount of heat energy required to reset the thermal diffusivity of the amplification material to an initial thermal diffusivity.

7. The sensor of claim 1, wherein the amplification material is at least one from a group consisting of: an organic bases molecule, a blended amine solvent, and polymer or metal-organic frameworks having an increase in target gas molar density compared to a molar density of the target gas in air.

8. The sensor of claim 1, wherein the semiconductor substrate is a silicon substrate, and
   wherein the sensing element includes a sensing wire positioned within the cavity and the amplification material encapsulates a portion of the sensing wire.

9. The sensor of claim 1, wherein the gas sensor is heated by passing a current through the sensing element.

10. The sensor of claim 1, further comprising:
    a heating element, wherein the gas sensor is heated by passing a current through the heating element for bringing the gas sensor into a predetermined temperature equilibrium state before measuring the thermal diffusivity of the amplification material.

11. A CMOS gas sensor, comprising:
    a sensing element;
    an amplification material coupled to the sensing element, and having a target gas dependent thermal diffusivity; and
    a semiconductor substrate having a cavity, the sensing element being positioned within the cavity,
    wherein the sensing element has a first resistance when the amplification material is exposed to a reference gas, and
    wherein the sensing element has a second resistance when the amplification material is exposed to a target gas; and
    a module converting a difference between the first resistance and the second resistance into a target gas concentration,
    wherein the amplification material is positioned around all of the sensing element such that the amplification material encapsulates the sensing element, and the sensing element is electrically connected to the module.

12. A thermal conductivity gas sensor, comprising:
    a sensing element;

an amplification material coupled to the sensing element, and having a target gas dependent thermal diffusivity; and a semiconductor substrate having a cavity, the sensing element being positioned within the cavity, wherein the sensing element measures the thermal diffusivity of the amplification material, wherein the amplification material is deposited on top of the sensing element and seals the top of the cavity without filling the cavity, and wherein the sensing element is a resistive transducer such that the sensing element has a first resistance when the amplification material is exposed to a reference gas and a second resistance when the amplification material is exposed to a target gas.

13. A CMOS gas sensor, comprising:

a sensing element;

an amplification material coupled to the sensing element, and having a target gas dependent thermal diffusivity; and a semiconductor substrate having a cavity, the sensing element being positioned within the cavity, wherein the sensing element has a first resistance when the amplification material is exposed to a reference gas, and wherein the sensing element has a second resistance when the amplification material is exposed to a target gas; and a module converting a difference between the first resistance and the second resistance into a target gas concentration, wherein the amplification material is deposited on top of the sensing element and seals the top of the cavity without filling the cavity, and the sensing element is electrically connected to the module.

* * * * *